United States Patent [19]
Foggia

[11] Patent Number: 5,111,831
[45] Date of Patent: May 12, 1992

[54] SCROTUM SUPPORTING CONDOM WITH RETENTION MEANS

[76] Inventor: David J. Foggia, 1505 SW. 6th, Portland, Oreg. 97207

[21] Appl. No.: 480,808

[22] Filed: Feb. 16, 1990

[51] Int. Cl.⁵ .......................... A61F 6/02; A61F 6/04
[52] U.S. Cl. ..................................... 128/842; 128/844; 128/918; 604/346; 604/347; 604/348; 604/349
[58] Field of Search ...................... 128/842, 844, 918; 604/346, 347, 348, 349; 2/21

[56] References Cited
U.S. PATENT DOCUMENTS

| | | |
|---|---|---|
| 2,392,049 | 1/1946 | Kunnucan . |
| 2,586,674 | 11/1949 | Lönne ................................ 128/844 |
| 3,631,857 | 1/1972 | Maddison ........................... 604/349 |
| 4,320,752 | 3/1982 | Comparetto ....................... 128/844 |
| 4,354,494 | 10/1982 | Hogin ................................ 128/844 |

FOREIGN PATENT DOCUMENTS 2586674 11/1949 Fed. Rep. of Germany .

Primary Examiner—Robert A. Hafer
Assistant Examiner—Brian E. Hanlon
Attorney, Agent, or Firm—William D. Haffner

[57] ABSTRACT

A rollable condom having a retention periphery at the open end (28) of an elongated tubular sheath (20). The open end (28) is a discontinuous periphery that communicates with a discontinuous bead (22) at its edge. The periphery becomes discontinuous at a notch (34). A hole (32) is located opposite the notch (34) within the sheath wall (38) along the bead (22). The hole (34) has an indentation (24) which is centered on the hole (32) toward the closed end (30) of the sheath (20). Located within the sheath (20) is an inner seal (36) which communicates with and protrudes from the sheath wall (38) to extend forward toward the closed end (30) of the sheath (20) to form a circumference of smaller diameter than the tubular sheath (20). When the sheath (20) is fully unrolled onto the penis, and the scrotum is positioned through the hole (32), a retention periphery is created which provides support to the scrotum in achieving increased physical contact during use.

21 Claims, 4 Drawing Sheets

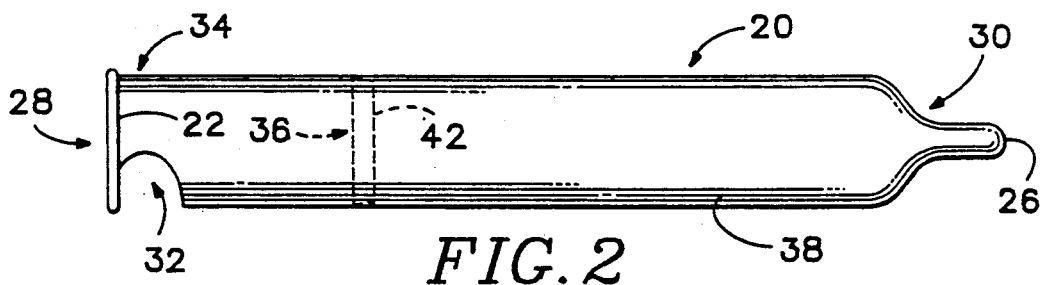
FIG. 1
FIG. 2
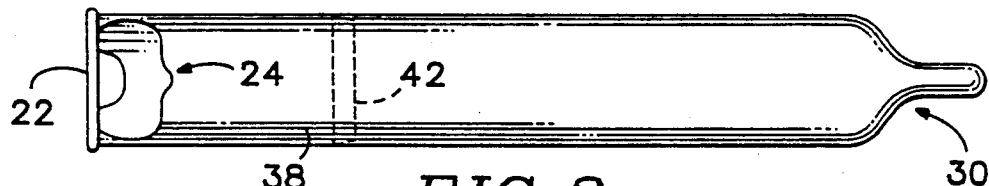
FIG. 3
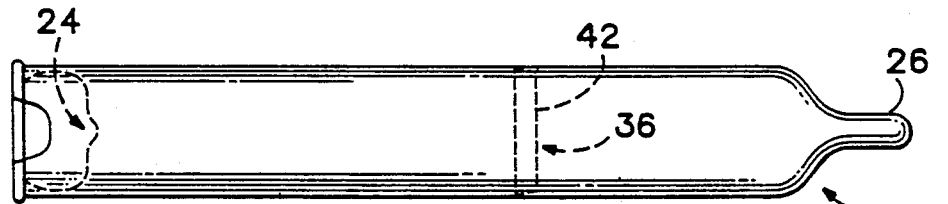
FIG. 4
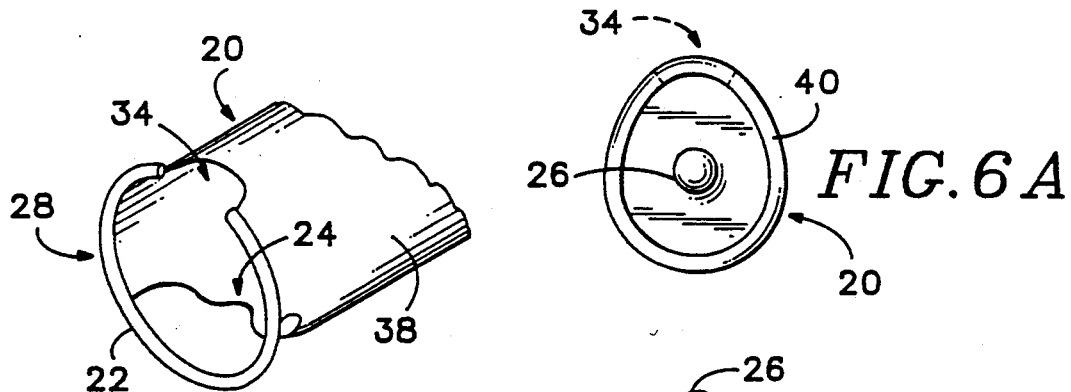
FIG. 5
FIG. 6A
FIG. 6B

SCROTUM SUPPORTING CONDOM WITH RETENTION MEANS

BACKGROUND-FIELD OF INVENTION

The present invention pertains to condoms, and more particularly, to a contraceptive or prophylactic sheath that provides a retention means at the open end of the condom. This retention means uses part of the condom's resilient wall and all of the elongated bead to secure the open end around the scrotum. This positions and supports the scrotum to increase the amount of physical contact it receives during sexual activity.

BACKGROUND-DESCRIPTION OF PRIOR ART

From the past to the present, rolled condoms have changed very little from their introduction. This has mainly occurred because a condom in the rolled disc shape is much easier to apply onto the erect penis when compared to an unrolled condom. Additionally, manufacturers favor rollable condoms because they allow for compact storage during packaging.

However, there are several problems that persistently arise with this traditional design. The first of which is the problem of condom slippage which often occurs during intense sexual activity. Generally the male is unable to sense the position of the condom because of his intensified sexual mood. Furthermore, during copulation sexual fluids are released which reduce friction and increase slippage. After sexual activity, the male may remove the condom only to find that it has slipped sufficiently to allow leakage.

A second problem with the traditional design is the pain caused from the rolled portion. Consequently, after one unrolls the condom onto the erect penis, an uncomfortable pain is discovered by the user at the base of the penis. This pain is caused by the pressure exerted against the skin by the rolled portion of the condom. Additional pain is received whenever pubic hair entangles with this rolled portion.

A third problem with traditional design is the inability to provide enough space for semen containment in the typical reservoir tip. After ejaculation, the reservoir tip usually becomes over-filled with semen. This can cause discomfort to the male by restricting the expulsion of the semen. But more importantly, the pressure caused from this over-filling exerts force against the condom wall. This force can weaken the condom wall. Additional force can be exerted against the wall through movements by the male or his sexual partner during pelvic thrusting. This also weakens the condom wall and increases the chance of leakage.

Still a further problem with the traditional rolled condom is its inability to affect the scrotum during use. It has been realized that stimulation of the male can be increased if the scrotum is touched during sexual activity. The design known today has virtually no affect on the scrotum and in fact, tends to reduce overall stimulation to the penis.

Additionally, a psychological problem can develop in the male from the combination of all these negative factors. Psychological stress can develop in the male who is concerned about these negative factors during use. This stress can distract the male and reduce the satisfaction gained from the sexual activity.

What is needed is a comfortable rollable condom that performs well and reduces psychological stress, while augmenting sexual stimulation of the scrotum during use.

Kunnican's 1946 U.S. Pat. No. 2,392,049 introduced the concept of an anchoring ring. This concept involves using the solid ring at the open end of a rollable condom. The ring is extended so as to encircle the scrotum during use. However, this concept has several problems.

The first problem is found when trying to install the condom onto the erect penis. The user may find it difficult to locate the scrotum hole in rolled position. The rolled condom would still have the traditional circular shape. Therefore, the user might have to fully unroll the condom before installing it onto the erect penis. Again, this would be a disadvantage because unrolled condoms are harder to install on the penis than rolled condoms.

Secondly, comfort is sacrificed because of the use of a solid ring around the scrotum. When a ring or continuous bead is used to encircle around this sexual organ, the pressure exerted against the skin is too strong. This creates an annoying feeling which is not supportive to the scrotum or its internal structures. It tends to distract the male during use.

Toward the end of use, after ejaculation, the male may encounter another problem. This design does not provide a reservoir tip for semen collection. If this was allowed to exist, and a penis was to take up the full length of this condom, semen leakage might result. This might occur because there would not be a tight ring at the base of the penis shaft. If pelvic thrusting were to continue after ejaculation, leakage by backflow toward the base of the penis could result.

After use, yet another problem is discovered. This is the problem of trying to remove the condom without pulling pubic hair. When the user grasps the ring from around the scrotum, there is an immediate tendency for the ring to roll forward toward the end of the penis. If the user has pubic hair, generally it will entangle within the roll and cause sharp pain to the user. Consequently, while this design could be used as a finger cot, it is not practical for use around the scrotum.

The rollable condom prescribed by Hogin in his 1982 U.S. Pat. No. 4,354,494 includes a retention strap for anchoring purposes of the condom to the penis. This retention strap is also located at the open end of the condom and is also stretched so as to encircle around the scrotum. However, this design has most of the same problems as Kunnican's above mentioned condom.

For example, if this condom is used in the dark or dimly lit locations, the user may be unable to correctly unroll the device. This is because a line of ink is used on the condom to indicate the position of the retention strap. Therefore, if one cannot see this line, one must guess and unroll the condom onto the erect penis.

Secondly, similar to Kunnican's condom, comfort is sacrificed. Hogin claims that his retention strap can be positioned so as to encircle the scrotum. Yet this retention strap is approximately half the size of Kunnican's ring. This reduced size would be even more uncomfortable to wear than Kunnican's condom.

Lastly, and again similar to Kunnican's condom, this condom would also tend to entangle with the pubic hair. This design also uses a ring which would roll forward when trying to remove the sheath from the penis. If the user has pubic hair it will entangle with this condom.

These prior art designs fail to meet the needs of the user. Both present the problem of trying to locate the position of the retention means when in the rolled position. Both present a retention means which is uncomfortable to wear and unsupportive to the scrotum. Furthermore, both interfere with the pubic hair to cause pain and discomfort. They are clearly nonfunctional for use around the scrotum. It should therefore be realized that a condom that could solve these problems and more, would be a significant advancement of the art.

SUMMARY OF THE INVENTION

In view of the above mentioned problems with traditional and prior art designs, it is a primary object of the present invention to provide a functional retention means which provides support to the scrotum in achieving increased stimulation during use.

A secondary object of the present invention is to provide an inner seal which can be used to both minimize semen leakage and enable rolling of the condom.

An additional object of the present invention is to provide the user with the ability to locate the scrotum hole in the rolled position, by using either the sense of sight or the sense of touch.

Yet another object of the present invention is to provide a design that can be rolled. Thus having the same advantages as rolled condoms.

A further object of the present invention is to provide a design which may function to keep the penis within the sexual orifice during use.

Additionally, a further object of the present invention is to provide extra space for semen containment after ejaculation.

Therefore, according to the present invention, the condom includes a resilient and flexible unitary body construction, having an elongate thin tubular sheath made of resilient material (i.e. latex rubber). The sheath is closed at one end and has an opening at the other end for entrance of the penis. The opening has a discontinuous periphery, preferably communicating with a discontinuous bead at its edge. A notch is formed where this periphery becomes discontinuous. Directly opposite this notch there is a hole in the sheath wall. At the forward end of this hole, toward the closed end of the sheath, there is an indentation with the shape of a half circle. An inner seal is also included within the tubular portion of the sheath which communicates with and protrudes from the sheath wall to extend forward toward the closed end of the condom. The thickness of this seal tapers to a point from its wider base to form an inner edge. This edge forms a smaller circumference than the tubular portion of the sheath.

The features of the present invention which are believed to be novel are set forth with particularity in the appended claims. The present invention, both as to its organization and manner of operation, together with further objects and advantages thereof, may best be understood by making reference to the following description taken in conjunction with the accompanying drawings in which like reference characters refer to like components in the several views.

BRIEF DESCRIPTION OF THE DRAWINGS

FIG. 1 is a side view of a conventional condom without the improvement of the present invention.

FIG. 2 is a side view of a condom with the embodiment of the present invention.

FIG. 3 is a bottom view of a condom with the embodiment of the present invention.

FIG. 4 is a top view of a condom with the embodiment of the present invention.

FIG. 5 is a perspective view of the opening end of a condom with the embodiment of the present invention.

FIG. 6A is a top view of a sheath with the embodiment of the present invention in rolled position.

FIG. 6B is a perspective view of a sheath with the embodiment of the present invention in rolled position.

Figure 7:
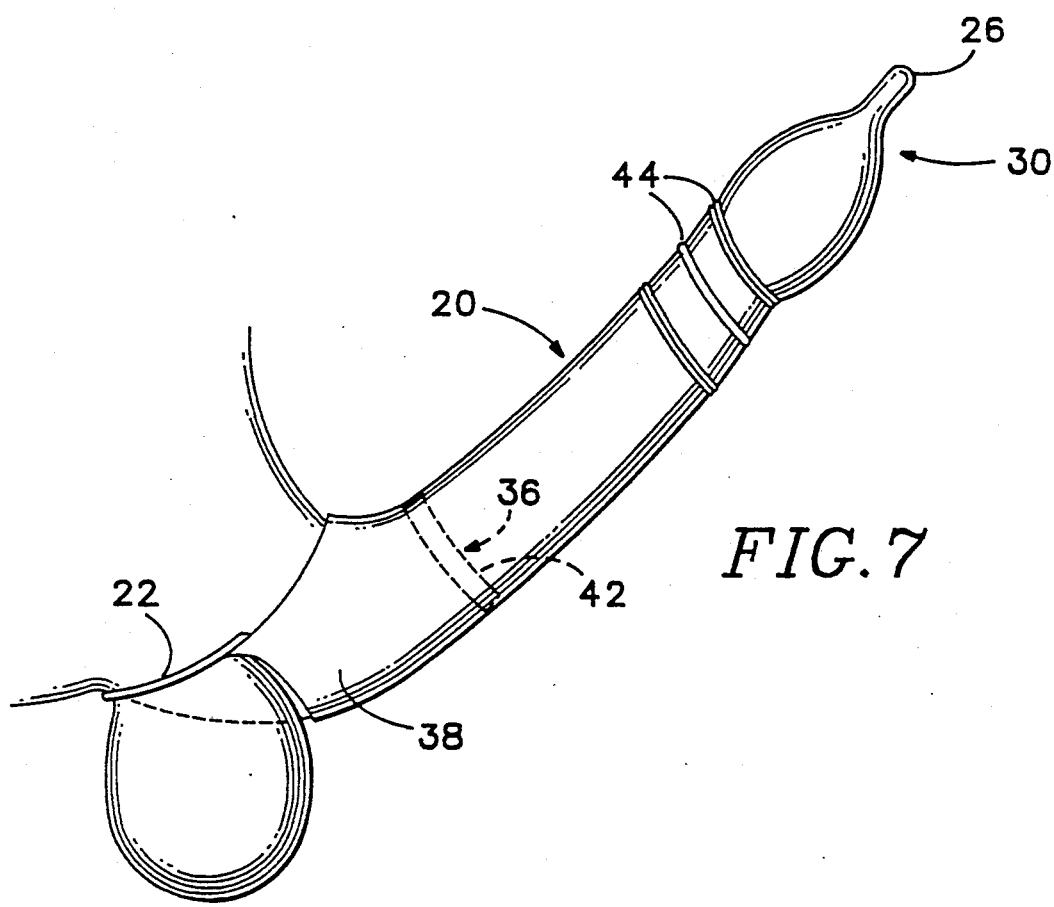
FIG. 7 is a perspective view of the present invention properly positioned on an erect penis.
Figure 8:
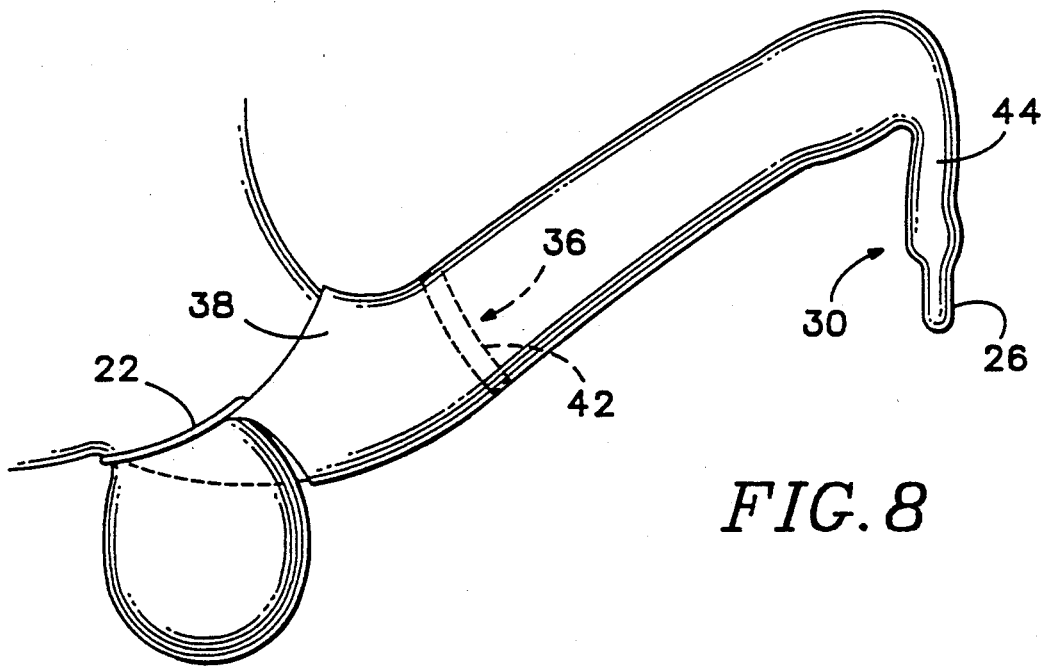
FIG. 8 is a perspective view of the present invention after being removed from the orifice, after ejaculation.
Figure 9:
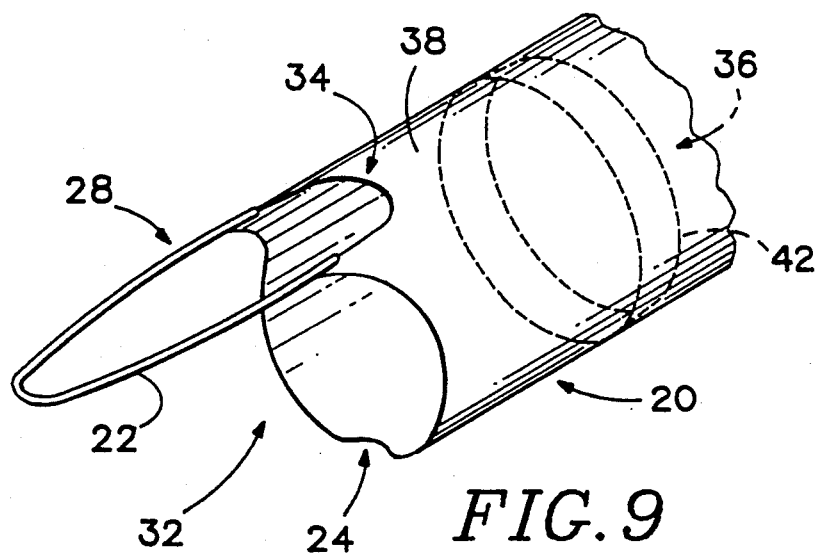
FIG. 9 is a perspective view of the open end of the present invention in a stretched position.
Figure 10:
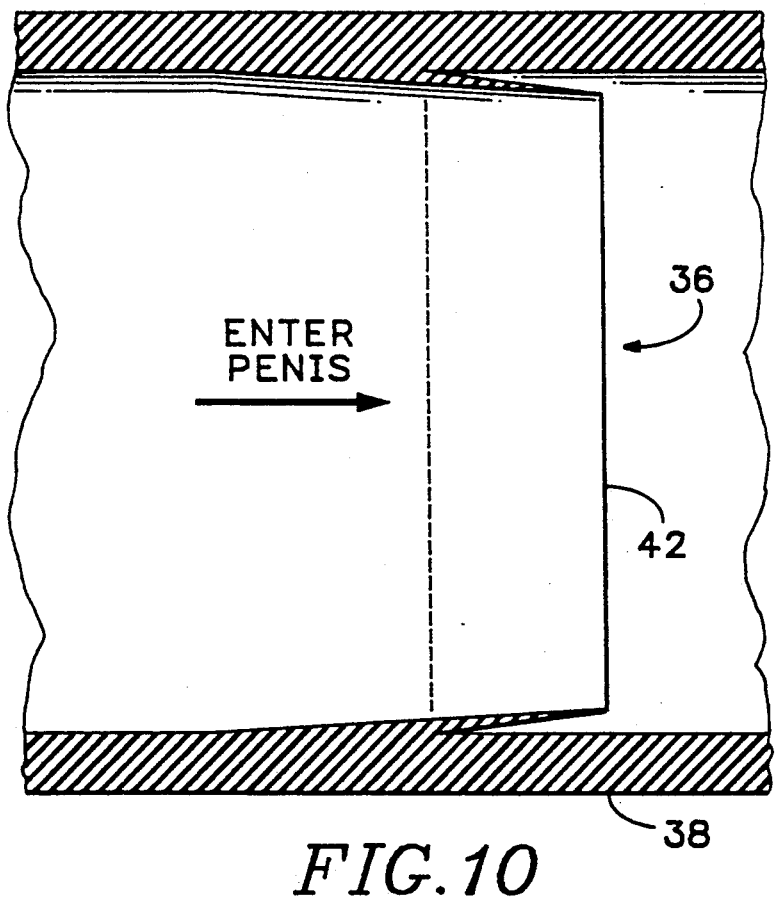
FIG. 10 is a cross sectional view of the inner seal of the present invention.

| List of Reference Numerals | |
|---|---|
| 20 Sheath | 22 Elongated Bead |
| 24 Indentation | 26 Resevoir Tip |
| 28 Open End | 30 Closed End |
| 32 Hole | 34 Notch |
| 36 Inner Seal | 38 Sheath Wall |
| 40 Rolled Portion | 42 Inner Seal Edge |
| 44 Excess Sheath Wall | 46 Right Gap |
| 48 Left Gap | |

DESCRIPTION OF THE INVENTION

While this invention is susceptible of embodiment in many different forms, there is shown in the drawings and will herein be in detail two specific embodiments with the understanding that the present disclosure is to be considered as an exemplification of the principles of the present invention, and is not intended to limit the invention to the embodiments illustrated.

FIG. 1 illustrates a full side view of a traditional condom without the improvement of the present invention.

Referring now to the drawings, and more particularly to FIGS. 2-10, there is illustrated a contraceptive or prophylactic sheath 20 which has open end 28 for receiving the male penis. Open end 28 has a discontinuous periphery, preferably communicating with a discontinuous elongate bead 22 at its edge. This opening periphery and its communicating bead 22 become discontinuous at a notch 34. A hole 32 is located opposite this notch within the sheath wall 38, along the bead 22. This hole has an indentation 24 which is preferably centered at the forward end of the hole toward closed end 30. An inner seal 36 communicates with and protrudes from sheath wall 38 to extend forward toward the closed end 30. The thickness of this seal tapers forward to a point from its wider base to form an inner seal edge 42. This seal edge forms an inner circumference which has a smaller diameter than the sheath 20.

DETAILED OPERATION OF THE INVENTION

To efficiently unroll the condom of the present invention onto the erect penis, the user first locates the position of notch 34. This can be accomplished through the use of either the sense of sight or the sense of touch.

Visually, in the rolled position, the condom of the present invention is egg-shaped instead of the traditional circular shape. The curved region having a smaller radius on this shape is where notch 34 is located. The curved region having a larger radius on this shape is where hole 32 is located. Therefore, the user should simply position the rolled condom so that the notch unrolls onto the upper side of the penis. Hole 32 will unroll along the underside of the penis.

A person can locate notch 34 in rolled position by feeling for the curved regions mentioned above. Additionally, the person can squeeze the rolled portion 40 to locate the position of notch 34. Again, this is where a portion of the elongate bead is missing from the periphery of the open end. When the person feels this area on the shape it is comparatively flat to the rest of the rolled portion. Again, the user should position the rolled condom on the end of the penis so that notch 34 will unroll onto the upper side of the penis.

Once the condom is fully unrolled, the user should extend bead 22 from the underside of the erect penis, to behind and around the scrotum. This causes sheath 20 to move toward the base of the penis and it immediately affects the scrotum by positioning it into a more sensitive position. During use, the retention means of the present invention supports the scrotum to stay in this more sensitive position where it receives more contact during sexual activity with the user's sexual partner. Increased stimulation to it and its internal structures results.

Accordingly, the fact that the present invention provides a functional retention means which not only works well as an anchor for rollable condoms, but that also provides support to the scrotum in achieving increased stimulation during use, is simply revolutionary. Furthermore, in its preferred embodiment, my invention has additional advantages in that it provides a retention means at the open end of a rollable condom where its expansion capacity can be enlarged during the manufacturing process, without increasing the diameter of the sheath.

it provides two ways to conveniently locate the position of the scrotum hole in rolled position.

it provides a seal on the interior of the condom that functions to roll with the sheath and stop leakage caused from semen backflow.

it increases safety by allowing excess sheath wall to extend past the penis during use. This has the combined effect of reducing end bursting and tearing of the condom, along with reducing the occurrences of leakage caused by semen backflow.

it provides a means for keeping the penis within the orifice during use.

Although the description above contains many specificities, these should not be construed as limiting the scope of the invention but as merely providing illustrations of some of the presently preferred embodiments of this invention. Consequently, there can be several changes made to the design of the present invention.

Figure 11:
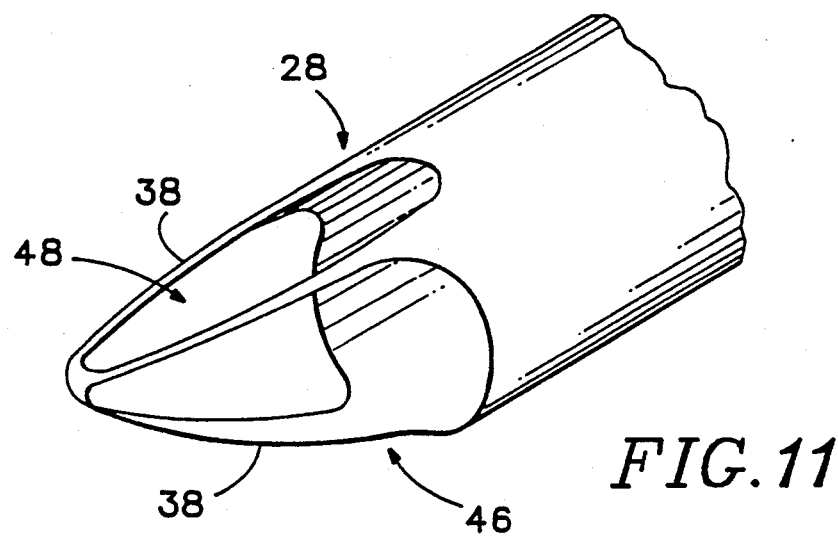
FIG. 11 is a perspective view of the open end of another embodiment of the present invention in a stretched position.
Figure 12:
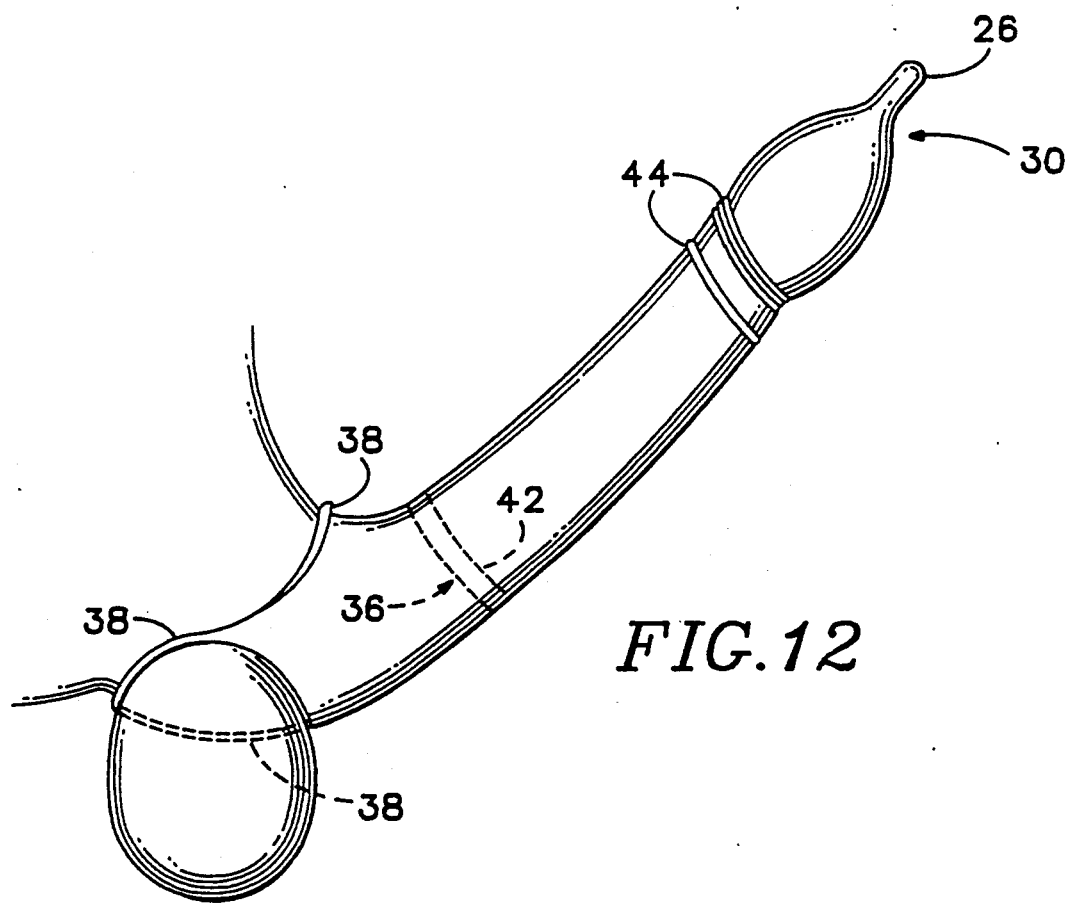
FIG. 12 is a perspective view of another embodiment of the present invention positioned on the erect penis.

The first of which can be seen at the area of the notch. This notch is where the continuous bead and usually an area of sheath wall is missing from the periphery of the open end. In stretched position, this functions to cause the retention periphery to pull on the scrotum at a different angle than the prior art designs. This angle minimizes interference by the retention periphery on the vas deferens. The angle can be achieved only by installing one or more notches around this opening periphery in combination with one or more holes for the scrotum (FIGS. 11,12).

Furthermore, the size and shape of the notch can be changed. If its size is enlarged during manufacturing, it increases the expansion capacity of the retention periphery. If it is made smaller, it decreases the expansion capacity of the retention periphery. Changing the shape of this notch tends to mainly affect the fit of the retention periphery over the pubic hair. This shape can be changed in many ways as long as it functions to make the periphery of the open end discontinuous.

Another area of change can occur at the edge of the open end. In the preferred embodiment, the edge of the open end is made up of part elongate bead and part sheath wall. However, this could be changed to include only sheath wall. Therefore, providing a band of wall to encircle the scrotum. Consequently, any shape between the circular nature of the bead and the flat nature of the sheath wall that will roll, can be used in combination with the above mentioned notch.

Another area of change can occur with the inner seal 36. In the preferred embodiment, this seal protrudes forward at an angle toward the closed end 30, with a tapered thickness. However, it can be changed to protrude at an even thickness from the sheath wall 38. This would still allow it to roll and would provide adequate strength. Additionally, it could be reversed to protrude at an angle toward the open end 28, with the same characteristics mentioned above. Furthermore, more than one seal could be added to provide an additional retention means for the sheath.

An additional variation of the present invention can be seen at the hole region as seen in FIGS. 11,12. This variation is to install two separate gaps opposite the notch in the sheath wall. Each gap can be used to encircle one testicle.

Furthermore, in the preferred embodiment of the present invention, the design should be manufactured to allow excess sheath wall 44 to extend beyond the erect penis in stretched position. This has several important functions.

First of all, by allowing excess sheath wall 44 to exist, pressure caused by semen build up after ejaculation is eliminated at the end of the sheath 20. Again, if this pressure is not reduced, it tends to weaken the sheath wall and can cause the sheath to burst open during use.

Secondly, by increasing the amount of sheath wall that extends beyond the end of the penis, the amount of space to contain the semen is also increased. This has the direct advantage of allowing the sheath a larger semen collection capacity than other condoms.

Thirdly, if this excess sheath wall is included and the condom is internally lubricated, the combined affect allows the penis to move within the sheath. This reduces wear on the sheath wall 38 in any one particular place. Again, this reduces bursting and tearing of the condom during use.

Additionally, if enough excess sheath wall 44 is included and allowed to accumulate within the sexual orifice, the condom can function to keep the penis within the sexual orifice during use. This occurs because of the tendency of the excess sheath wall 44 to stick to the inside of the orifice. The sexual fluids along with the muscular contractions within the orifice tend to increase this effect.

Thus, the scope of the present invention should be determined by the appended claims and their legal equivalents, rather than the examples given.

I claim:

1. A condom comprising:
   (a) an elongate thin-walled tubular sheath of resilient material being closed at one end and having an opening at the other end, said opening including a discontinuous periphery with a discontinuous elongated bead at its edge;
   (b) retention means for retaining said condom in place during use located in said periphery; and
   (c) tactile identification means, in said periphery where said periphery and said bead are discontinuous, for locating said retention means when the condom is rolled.

2. A condom according to claim 1 wherein said opening comprises one or more sections of said elongated bead around said edge.

3. A condom according to claim 1 wherein said periphery comprises one or more retention means.

4. A condom according to claim 1 wherein said retention means provides support to the user's scrotum to achieve increased physical contact during use.

5. A condom according to claim 1 wherein said retention means comprises one or more holes in the wall of said sheath.

6. A condom according to claim 5 wherein said hole within said sheath includes an indentation at the end of said hole nearest the closed end of said sheath for improving the fit of said sheath in its stretched position over the user's outer urethra.

7. A condom according to claim 1 wherein said tactile identification means comprises a notch located opposite said retention means in said periphery.

8. A condom according to claim 7 wherein said notch prevents pubic hair entanglement during removal of said sheath.

9. A condom according to claim 1 further comprising visual identification means for locating said retention means when said condom is rolled.

10. A condom according to claim 1 further comprising a seal which protrudes from and communicates with the interior wall of said tubular sheath; said seal protruding at an angle toward the closed end of said tubular sheath for an equal distance from the point of protrusion around the inner circumference of said tubular sheath; the circumference of said forms a smaller diameter than the inner circumference of said tubular sheath.

11. A condom comprising:
   (a) an elongate thin-walled tubular sheath of resilient material being closed at one end and having an opening at the other end, said opening including a discontinuous periphery with a discontinuous elongated bead at its edge;
   (b) retention means for retaining said condom in place during use located in said periphery; and
   (c) identification means for locating said retention means when the condom is rolled.

12. A condom according to claim 11 wherein said identification means comprises tactile identification means located in said periphery where said periphery and said bead are discontinuous.

13. A condom according to claim 12 wherein said tactile identification means comprises a notch located opposite said retention means in said periphery.

14. A condom according to claim 13 wherein said notch prevents pubic hair entanglement during removal of said sheath.

15. A condom according to claim 11 wherein said identification means comprises visual identification means.

16. A condom according to claim 11 wherein said opening comprises one or more sections of said elongated bead around said edge.

17. A condom according to claim 11 wherein said periphery comprises one or more retention means.

18. A condom according to claim 11 wherein said retention means provides support to the user's scrotum to achieve increased physical contact during use.

19. A condom according to claim 11 wherein said retention means comprises one or more holes in the wall of said sheath.

20. A condom according to claim 19 wherein said hole within said sheath includes an indentation at the end of said hole nearest the closed end of said sheath for improving the fit of said sheath in its stretched position over the user's outer urethra.

21. A condom according to claim 11 further comprising a seal which protrudes from and communicates with the interior wall of said tubular sheath; said seal protruding at an angle toward the closed end of said tubular sheath for an equal distance from the point of protrusion around the inner circumference of said tubular sheath; the circumference of said forms a smaller diameter than the inner circumference of said tubular sheath.

* * * * *